United States Patent
Hammond

(10) Patent No.: US 6,957,738 B2
(45) Date of Patent: *Oct. 25, 2005

(54) EMERGENCY RELIEF SYSTEM

(75) Inventor: David A. Hammond, Tinton Falls, NJ (US)

(73) Assignee: DLH, Inc., Tinton Falls, NJ (US)

( * ) Notice: Subject to any disclaimer, the term of this patent is extended or adjusted under 35 U.S.C. 154(b) by 342 days.

This patent is subject to a terminal disclaimer.

(21) Appl. No.: 09/963,734

(22) Filed: Sep. 26, 2001

(65) Prior Publication Data

US 2002/0104774 A1 Aug. 8, 2002

Related U.S. Application Data

(63) Continuation of application No. 09/596,157, filed on Jun. 16, 2000, now abandoned, which is a continuation-in-part of application No. 09/326,837, filed on Jun. 7, 1999, now abandoned.

(51) Int. Cl.[7] .............................................. B65D 69/00
(52) U.S. Cl. .................... 206/570; 206/425; 206/459.5; 206/438; 206/803
(58) Field of Search .............................. 206/570, 571, 206/572, 576, 803, 459.5, 38, 425, 438

(56) References Cited

U.S. PATENT DOCUMENTS

| | | | | |
|---|---|---|---|---|
| 752,463 A | * | 2/1904 | Morris | 217/5 |
| 1,090,553 A | * | 3/1914 | Mashek | 190/109 |
| 1,487,014 A | * | 3/1924 | Davis | 206/570 |
| 2,324,194 A | * | 7/1943 | Campiglia | 224/623 |
| 3,958,690 A | * | 5/1976 | Gee, Sr. | |
| 5,169,001 A | * | 12/1992 | Scheibel | 206/425 |
| 5,931,304 A | * | 8/1999 | Hammond | 206/570 |
| 6,460,702 B2 | * | 10/2002 | Hammond | 206/570 |

OTHER PUBLICATIONS

Prior Art First Aid Kit #1–#6.*
National Safety Council First Aid Guide Book.*
European Search Report established for EP 00 96 1984 on Feb. 6, 2004.*

* cited by examiner

*Primary Examiner*—Jila M. Mohandesi
(74) *Attorney, Agent, or Firm*—Gardner Carton & Douglas LLP

(57) ABSTRACT

The first aid kit of the present invention includes a case that includes means for providing quick access to the contents carried by the case. The case further provides, on the inside, a plurality of regions, defining compartments, arranged in an accordion style columnar array. Contained in the compartments are packs which are specifically designed with products appropriate for a particular first aid situation arranged according to a system of medical priorities following the principle of triage, from the most serious to the least serious first aid situation. The first aid kit further provides an guidebook that contains detailed instructions regarding the products contained in each pack as well as instructions on use of the products for different types of first aid situations. The first aid kit further includes an overview card that is an overview of the components of the first aid kit, identifying each of the packs for quick reference in a first aid situation. Each of the packs contains medical products specifically selected for different types of first aid situations as well as an instructional card that gives quick reference instructions for administration of first aid in these situations.

10 Claims, 10 Drawing Sheets

EMERGENCY RELIEF SYSTEM

This is a Continuation Application of U.S. patent application Ser. No. 09/596,157, filed Jun. 16, 2000, now abandoned that is, in turn, a Continuation-in-Part Application of U.S. patent application Ser. No. 09/326,837 now abandoned filed Jun. 7, 1999.

FIELD OF THE INVENTION

The present invention relates in general to first aid kits and, in particular, to a first aid kit which is adaptable to a plurality of first aid environments.

BACKGROUND OF THE INVENTION

A key element for rapid decisive care in first aid is the instant recognition and management of the most serious injuries first. Organizations such as the American Red Cross and the National Safety Council spend considerable amounts of time during classroom training attempting to reinforce this principal. Unfortunately, in many cases, for example, the initial reaction of the responder is to simply provide first aid for the most obvious injury and, as an after thought, check the victim's pulse. Additionally, most first aid kits of the prior art present first aid supplies individually, in an often times confusing planar array. Thus, a first aid responder must select each first aid supply individually.

What would thus be advantageous is a first aid kit that was adapted for use in a wide variety of different types of first aid situations. Such a kit would also appeal to a diversity of users by ease in selection and usage of the supplies. Such a kit would appeal to a diversity of uses by ease in selection and usage of the instructions. Such first aid kit would provide quick access to the appropriate medical products for a given type of first aid condition. Such kit would further provide quick access to information regarding different first aid situations so that the users could appropriately and properly use the supplies found in the kit.

SUMMARY OF THE INVENTION

The emergency relief system, or, equivalently, first aid kit, of the present invention includes a first kit comprising a carrying case that includes means for providing quick access to the contents carried by the case. The carrying case further provides, on the inside, a plurality of compartments arranged in sequence to obtain a columnar array providing a card catalogue/file cabinet-like effect. Contained in the sequential compartments are first aid packs which are specifically designed with products and instructions appropriate for a particular first aid situation. The first aid kit further provides a guidebook that contains detailed instructions regarding the products contained in each pack as well as instructions on use of the products for different types of first aid situations. The first aid kit further includes an overview card that includes an overview of the components of the first aid kit, identifying each of the packs, for quick reference in a first aid condition. Additionally, each of the packs contains medical products specifically selected for different types of first aid situations as well as an instructional card that gives quick reference instructions for administration of assistance in these situations.

In one embodiment of the present invention, each of the packs is designated a color for a first aid situation which is different than the colors designated for other first aid situations, for example, BLUE is associated with the breathing pack. The overview card is likewise color coordinated to assist the user in quickly finding the appropriate pack for the type of first aid situation encountered. The guidebook is color coordinated with the packs such that the detailed first aid instructions are found on pages which have borders matching the color of the pack. The guidebook parallels the instruction cards in each pack.

In still a further preferred embodiment, in addition to color coordinating the packs, each pack is designated by a unique icon that is recognizable in any language. The icons are utilized within the detailed guidebook as well as on the first aid kit overview card. Additionally, the instructional cards contained in the packs as well as the detailed instructions contained in the guidebook are set forth in graphical depictions to guide the user in the use of the medical products in the type of first aid situation encountered. Furthermore, the instructional cards contained in the packs are capable of being combined to form a guidebook such that a secondary responder can read the matching instructions on the instructional card to a primary responder who can follow the guidebook graphical depictions simultaneously. This process saves time and increases accuracy in rendering first aid.

To aid consumers, who have less formal training, the columnar array providing the card catalogue/file cabinet-like effect may be further expanded to present all the necessary packs in an accordion style columnar array. Thus, using this design, the primary emergency responder is rapidly able to completely visualize all of the packs as they fan out in front of them. This enables the responder to visualize all of the supplies, organized by injury, at once in an easy to comprehend array. This is contrasted with the confusing planar arrays of the prior art, which do not present first aid supplies packaged by injury. For the untrained responder, the structure of the first aid kit of the present invention provides a FUNCTIONAL INTELLEGENCE™ approach, because the structure guides the user through the principles of administering first aid.

The triage principle is the sorting of and allocation of treatment to patients according to a system of priorities designed to maximize the number of survivors in an emergency situation. Therefore, the order and sequence of the packs within the first aid kit is designed and assembled in the order of clinical or medical response. This design is advantageous because it ensures that, regardless of the visible injury, basic life support checks are performed first on every victim. For example, even if the responder comes upon a bone injury and selects that pack first, the integration of the triage principle with the bone pack directs the responder back to the basic life support check. Additionally, the first aid kit of the present invention provides a blueprint approach that further reduces hesitation and errors of omission during an emergency response. This is accomplished through the integrated use of colors, icons and numbers throughout all the packs. Furthermore, the present invention may include trouble-shooting causative indicating graphics depicting the types of injuries each pack is used for; e.g., the specific types of injuries for which the bleeding pack may be used.

In a further embodiment, the present invention's design is also useful for environmental specific first aid needs such as home use, auto use and pet first aid.

In a yet further embodiment, to assist in the area of aiding children, for example, in using the present invention, the first aid kit may include a "see through" top. This kit can further include a "pop up" feature identifying an injury character icon that is activated when the top is withdrawn, or alternately, the organizational scheme of the first aid kit can be printed on the top.

In yet a further embodiment, each pack is mechanically keyed according to the different clinical response required. For example, the BLUE pack can have a different shape and size than the PURPLE, RED or YELLOW packs, thereby ensuring that the packs cannot be confused with one another.

In yet a further embodiment, to assist users who are visually impaired, enlarged print Braille characters may be included on pack labels, overview cards, instructional cards, and in the guidebook.

DETAILED DESCRIPTION OF THE PREFERRED EMBODIMENT

Figure 1:
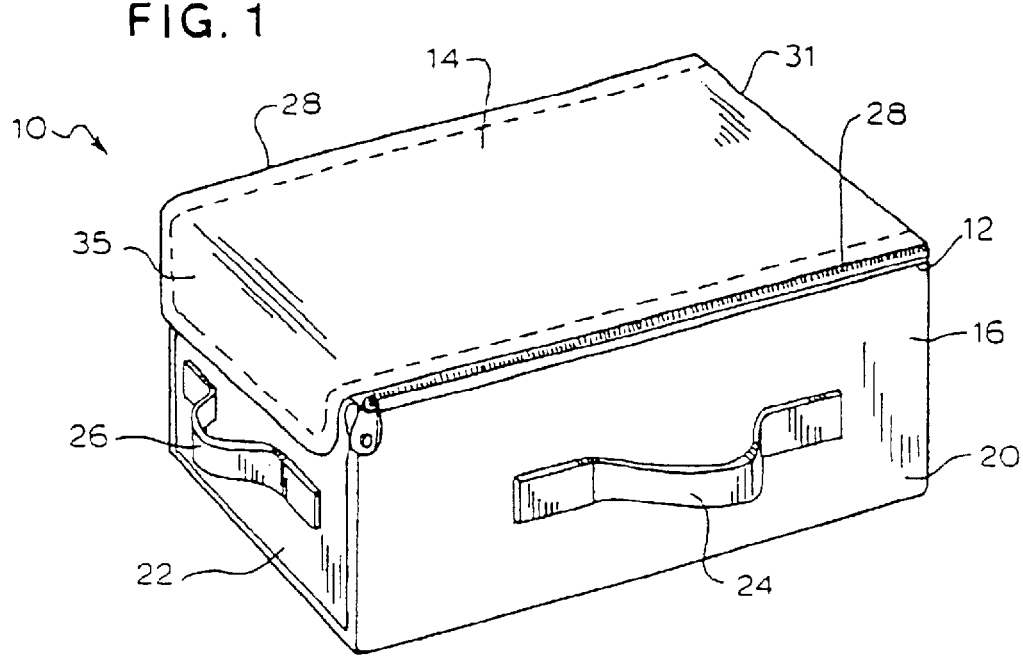
FIG. 1 is a perspective view of a first aid kit made in accordance with the principles of the present invention.

Referring first to FIG. 1, a perspective view of a first aid kit 10 made in accordance with the principles of the present invention is seen. The first aid kit 10 is carried in a case 12 that has a top 14 and a base 16 having a bottom, two sides 20, and two ends 22. The sides 20 of the base 16 are generally rectangular and the ends 22 of the base 16 are generally square. The first aid kit 10 of the present invention is preferably made of a lightweight material to enable ease of carrying. In the preferred embodiment, the first aid kit 10 is made of a flexible material such as nylon. In an alternative preferred embodiment, the kit 10 can be made of a rigid, lightweight material such as plastic.

To further aid in carrying, the first aid kit 10 is provided with a handle 24. In the preferred embodiment, a handle 24 is provided on a side which enables the user to carry the first aid kit in a generally horizontal orientation. Additionally, a handle 26 can be provided on the end of the first aid kit that enables the user to carry the first aid kit in a vertical orientation. Alternatively, a shoulder strap (not shown) can be provided alone or in combination with a handle.

Figure 2:
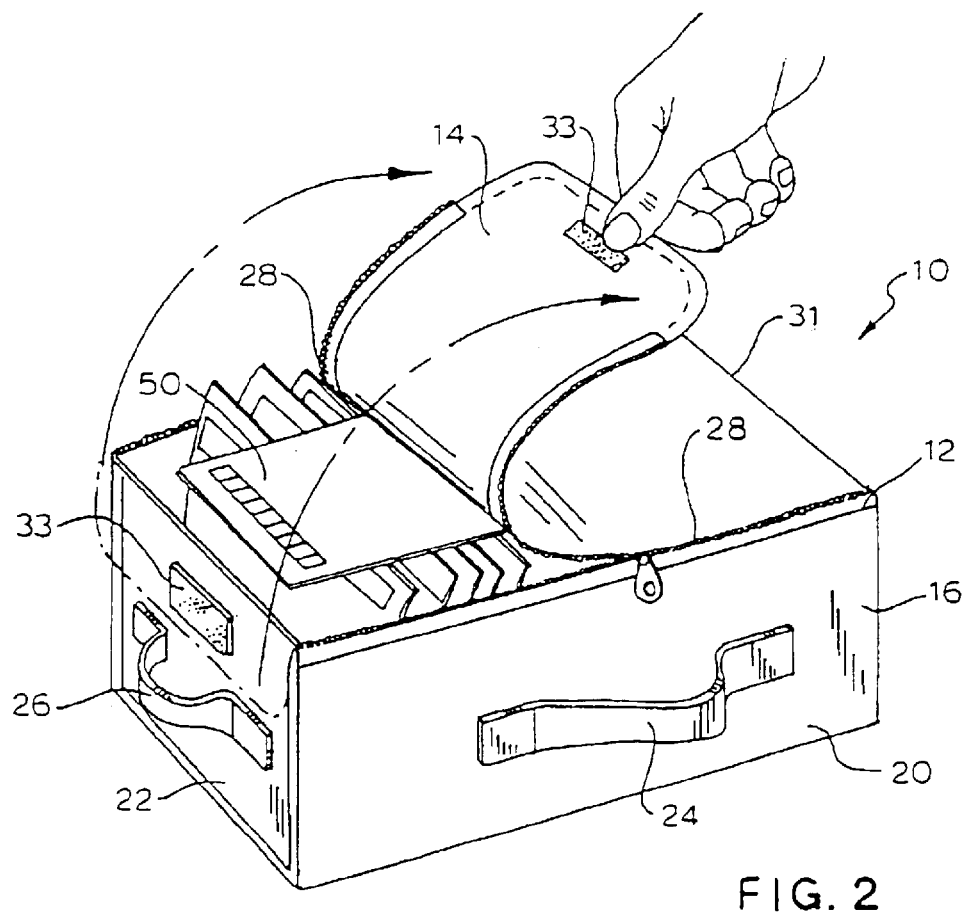
FIG. 2 is a perspective view of the first aid kit of FIG. 1 showing a user opening the first aid kit for access to the contents.

The top 14 is secured to the base 16 by use of a closure means for enabling quick access to the contents of the first aid kit 10. In a preferred embodiment, the closure means consist of a pair of zippers 28 that secure the top 14 to the sides 20. A first end of the top 14 is secured to the base by a living hinge 31 integrally formed with that end of the base 16. The end of the top 14 opposite the living hinge 31 is secured to the base 16 by a hook and loop style fastener 33 contained on an over-flap 35. Thus, in use, a user simply pulls the over-flap 35 over the top 14 thereby releasing the hook and loop fastener 33. On further pressure upward and rearward, the zippers 28 are automatically opened thus provided quick access to the content of the first aid kit 10, as seen in FIG. 2.

Figure 3:
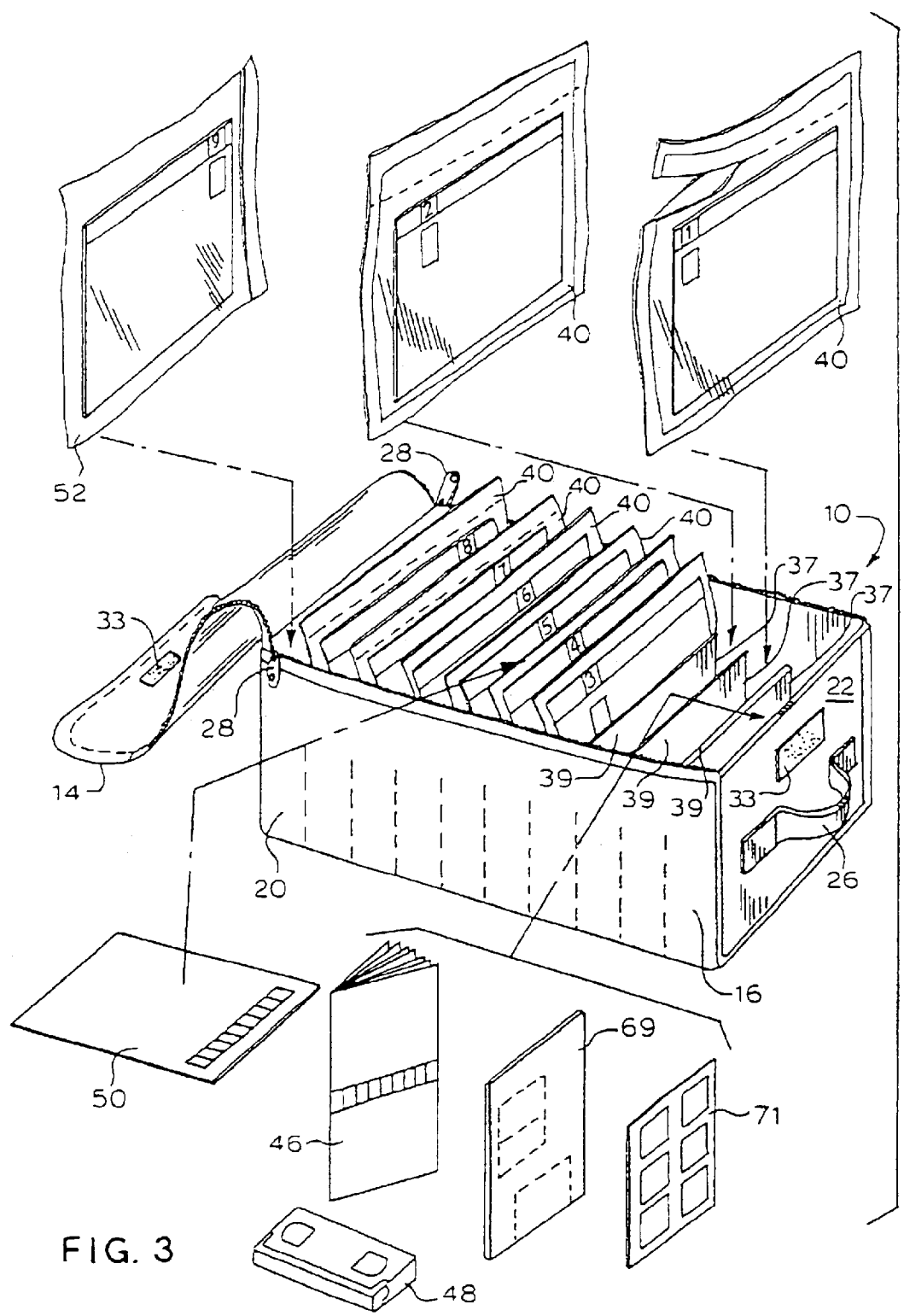
FIG. 3 is an exploded view of the contents and orientation of a first aid kit made in accordance with the principles of the present invention.

Referring to FIG. 3, the base 16 of the first aid kit 10 defines a plurality of compartments 37. Each compartment 37 is sequentially oriented in front of the subsequent compartment. By so orienting the compartments 37 in this manner, a card catalogue/file cabinet like effect is provided in which contents can be carried in each compartment 37 in an easy to identify upright position. Additionally, in each of the compartments 37, flexible walls 39 are used such that contents of different thickness can fit into each of the compartments 37.

The contents of the first aid kit 10 include a plurality of packs 40. Each of the packs 40 consist of a plastic bag 42, an instructional card 44 and a plurality of medical supplies provided for specific types of first aid situations. The first aid kit 10 further contains a detailed guidebook 46, which explains the use of the medical products in different types of first aid situations. In a further preferred embodiment, the first aid kit 10 contains an instructional guide 48 in video and/or audio format, which helps train the user on the use of the first aid kit 10. A card 50 is provided which contains an overview of the first aid kit 10.

In one embodiment, the packs 40 may be arranged in the compartments 37 in an order based on the seriousness of the injury, or type first aid situation, for which the medical supplies in a pack are provided. Thus, when the first aid kit 10 is opened to provide access to the contents of the first aid kit 10, the compartment 37 closest to a first aid emergency responder using the first aid kit 10 may contain a pack 40 that contains medical supplies for treating the most serious type of injury. The next compartment 37 in sequence may contain a pack that contains medical supplies for treating the next most serious type of injury, and so on. Thus, the first aid kit 10 of the present invention provides a structure such that packs 40 may be organized in the first aid kit 10 in order of injury seriousness, thus providing a structure that emulates the principles of triage.

The first aid kit further contains a magnetic card 69, which includes magnetic identifiers, a locator for the first aid kit, and a card having background medical information regarding family members. Further, a plurality of self-adhesive identifiers 71 are provided which can be placed in various locations, such as in kitchen cabinets, bathroom cabinets and the like, to quickly identify where the first aid kit 10 is stored. Still further, the guidebook 46 contains a page for the user to fill in information about emergency numbers and particular family health conditions.

The packs 40 contain specific medical supplies designed for specific types of first aid situations. In the preferred embodiment described herein, the different first aid situations include breathing, bleeding, shock, head and spine, bone, eye, burn and bites and stings. An instructional card 73 is provided for each of the different types of packs. The instructional card 73 for each pack 40 is color coordinated in a color unique to and different from the colors for the remaining packs 40. In addition, the overview card 50 utilizes these colors to identify the different packs 40 and the guidebook 46 sets forth the instructions for each of the different types of procedures based on pages which are bordered in a coordinated color.

For example, in the preferred embodiment described herein, a breathing pack is coordinated with the color blue, the bleeding pack is coordinated with the color red, the shock pack is coordinated with the color gold, the head and spine pack is coordinated with the color teal, the bone pack is coordinated with the color brown, the eye pack is coordinated with the color navy blue, the bum pack is coordinated with orange, the bite and sting pack is coordinated with the color magenta, and the extras pack is coordinated with the color gray. In addition, the guidebook 46 contains instructions for first aid conditions in which specific medical products are not used, such as, for example cardiopulmonary resuscitation (CPR). In the preferred embodiment, the CPR instructions are color coordinated purple. Additional instructions in the guidebook 46 include what to do if poison is ingested. The poison is color coordinated as green. In an alternative preferred embodiment, the packs 40 contained in the compartments 37 include, in sequential order, instructional cards for CPR and poison.

In addition to the color coordination, the packs 40, guidebook 46 and overview card 50 employ icons for each of the first aid situations addressed. Thus, the icon for the breathing pack is a graphic depiction of the breathing channels in a human, the icon for the bleeding pack is drops of blood, the icon for the shock pack is a lightning bolt, the icon for the head and spine pack is a human head, the icon for the bone pack is a broken bone, the icon for the eye pack is an eye, the icon for the burn pack is a flame, the icon for the bites and stings pack is a bee, and the icon for the extras pack is a bandage strip and scissors. In addition, the guidebook 46 and instructional card 73 for CPR include an icon which is an electrocardiogram line while the guidebook 46 and instructional card 73 for the poison include an icon which is a skull and crossbones. In an alternate embodiment, a different cartoon character may be used for each icon used to identify each of the first aid situations addressed by each of the packs 40 in the first aid kit 10.

Figure 4:
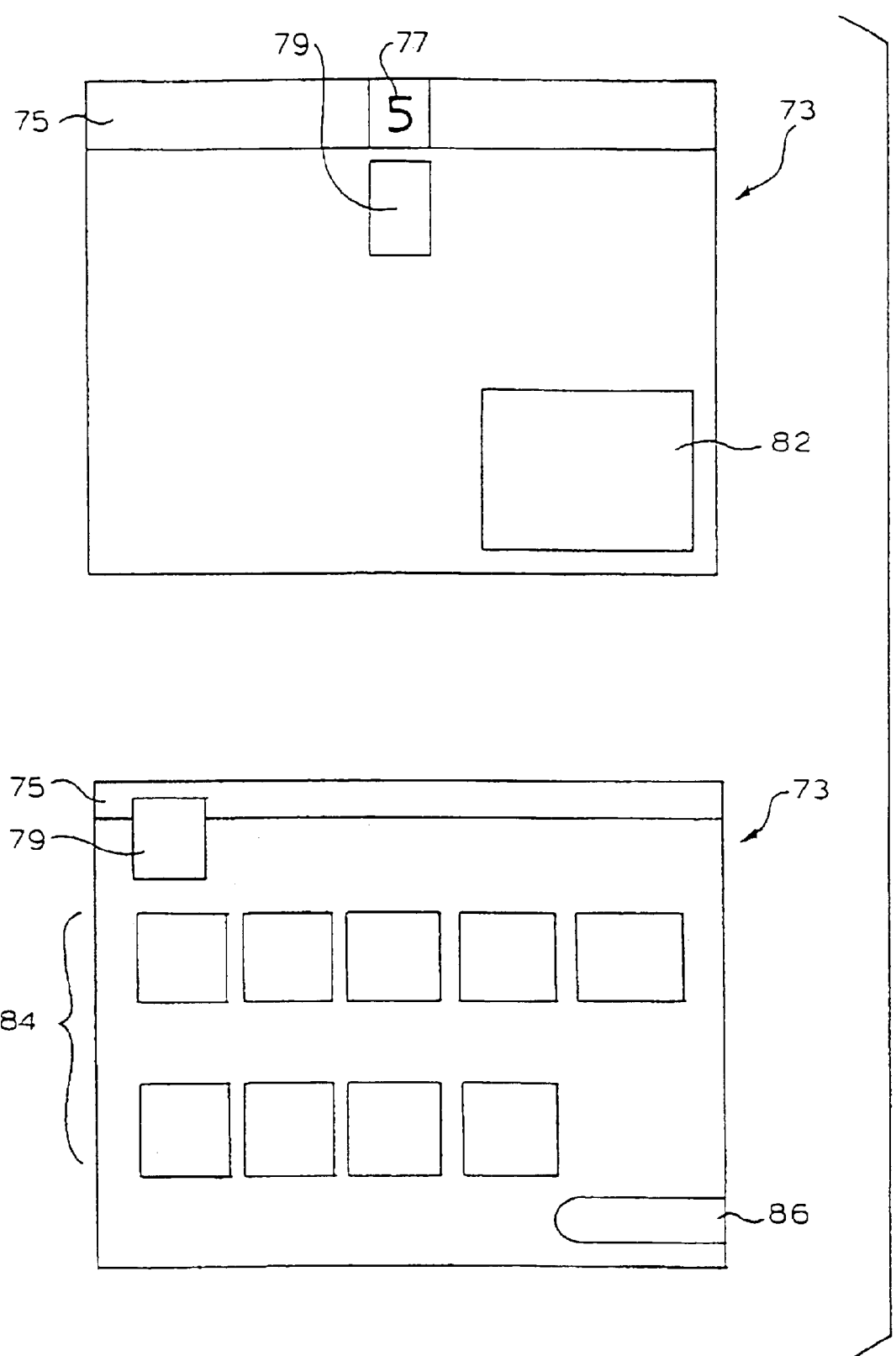
FIG. 4 is an exemplary card made in accordance with the principles of the present invention.

It is a particular advantage of the present invention that the instructional cards 73 for each pack are oriented with information in the same area of the card 73. Thus, once familiarized with the first aid kit 10, the user knows where to find appropriate information on any of the cards 73. Referring to FIG. 4, an exemplary instructional card 73 is seen which is made in accordance with the principles of the present invention. The upper edge of the card, which is visible to the user when the pack is carried in the card catalogue/file cabinet type orientation of the carrying case, sets out an identification of the type of pack on a band 75 of the coordinated color. The sequential number 77 of the pack 40 is also identified so that if the user is colorblind, the user can easily recognize, as well as replace and reorder the packs 40 as explained in detail below. The sequential numbers 77 are offset from each other, as seen in FIG. 3, to further enhance to the card catalogue/file cabinet like effect. Additionally, positioned underneath the band of color coordination 75 is the icon 79 for the particular pack 40. In the lower right portion of the of the card is an inventory 82 of the medical products in the pack 40.

Contained on the opposite side of the card 73 are instructions for use of the products contained in the pack 40. Again, along the upper edge of the card visible to the user when in the carrying case is a band of the coordinated color 75. Also positioned in the upper left-hand corner of the backside of the card is the icon 79. Positioned underneath the color-coordinated band 75 is a series of step-by-step instructions 84, including a series of graphical instructions, on using the contents of the pack 40. Positioned in the lower right-hand corner of the instructional card 86 is a toll-free number to call to reorder the pack 40, as explained in more detail below.

Utilizing this format, the packs 40 include contents directed toward specific first aid situations, as well as instructional cards 73 to direct the user how to use the products to care for the injured patient. In order to use one of the packs 40, the user opens the pack 40 along a tear line 88 that is provided on the pack 40. The pack 40 is provided sealed to maintain the sterility of the contents of the pack 40 while the tear line 88 allows the user easy access to the pack 40. In the preferred embodiment described herein, the tear line 88 is made according to the description provided in U.S. Pat. No. Re. 30,726, the disclosure of which is incorporated herein.

In the alternate preferred embodiment of the present invention, the instructional cards 73 contained in the packs are capable of being combined to form a guidebook (not shown) such that a secondary responder can read the matching instructions on the instructional card to the primary responder who can follow the guidebook graphical depictions simultaneously. The guidebook 46 would duplicate the instruction cards 73 in each pack.

Figure 5:
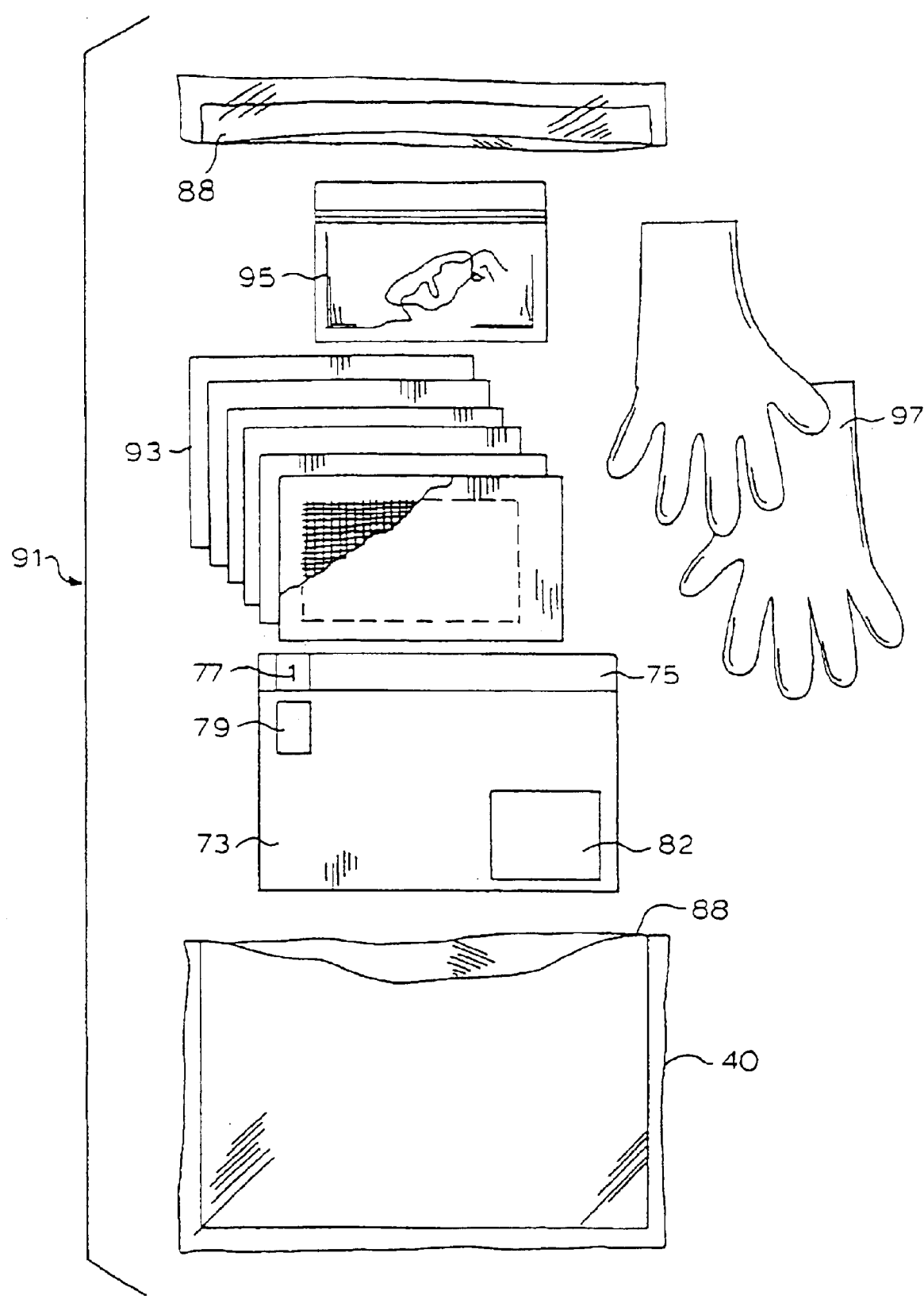
FIG. 5 is an exploded view of one of the packs of the first aid kit of FIG. 1.

Referring to FIG. 5, the breathing pack 91 is depicted as an exemplary example of the packs 40. The breathing pack 91 includes gauze sponges 93 which are used to clean fluid, saliva, etc. from around the mouth; a mouth guard 95 to allow for mouth-to-mouth resuscitation while avoiding mouth-to-mouth contact; and disposable medical gloves 97 to reduce contact with body fluids. The bleeding pack includes gauze sponges to control bleeding, a rolled bandage to hold gauze in place, cloth tape to hold the bandages and gauze in place, larger bandages which are used in combination with the bandages on larger wounds and disposable medical gloves to reduce contact with body fluids. The shock pack includes a thermal blanket. The head and spine pack include gauze sponges to control bleeding, a rolled bandage to hold the gauze in place, cloth tape to hold bandages in place, and disposable gloves to reduce contact with body fluids.

Figure 6:
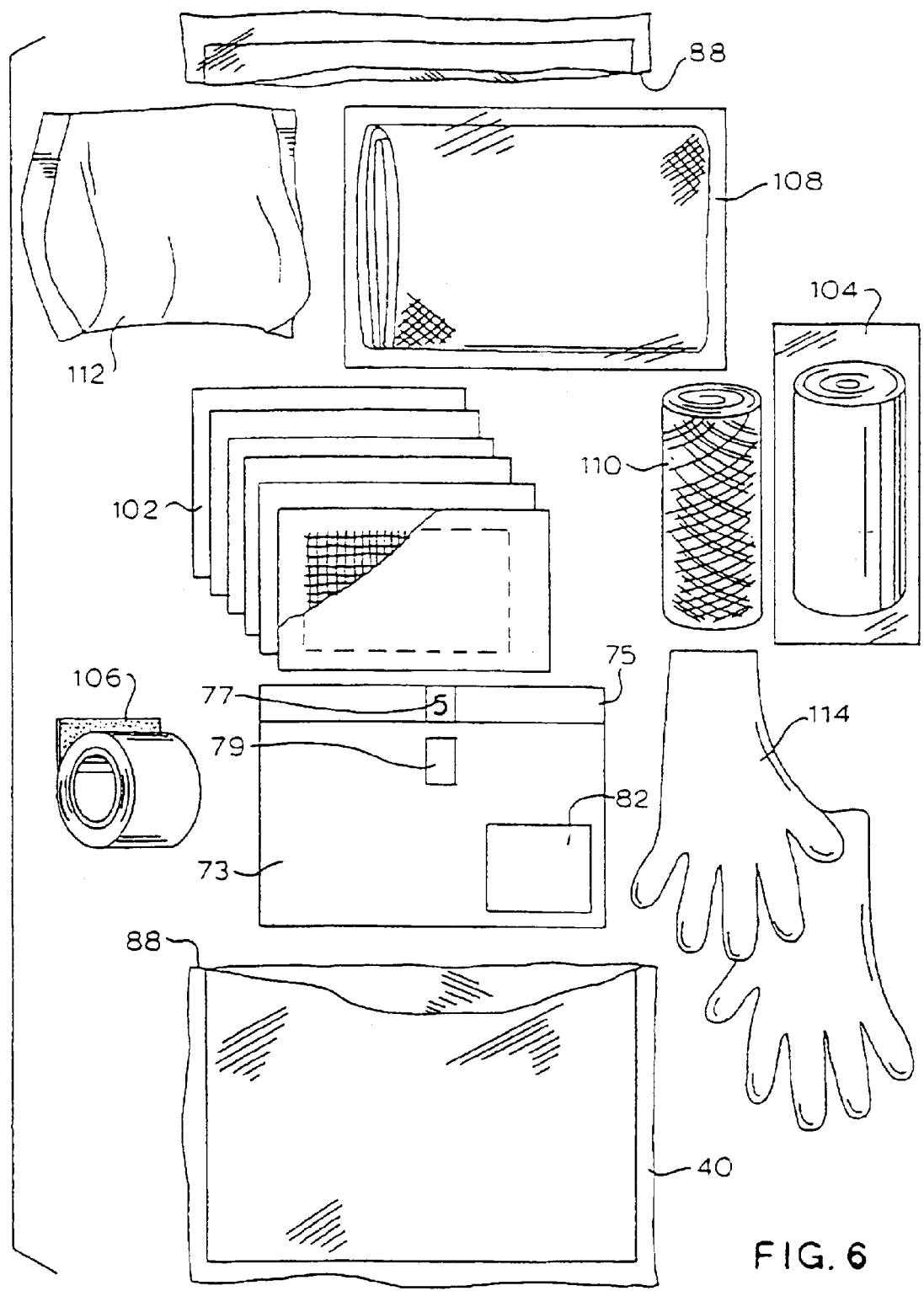
FIG. 6 is an exploded view of another of the packs of the first aid kit of FIG. 1.

Referring to FIG. 6, the bone pack 100 is depicted as a further exemplary example of the packs 40. The bone pack includes gauze sponges 102 which are used to control bleeding, rolled bandage 104 used to secure the splint and to hold the gauze in place, cloth tape 106 used to hold the gauze and splint in place, triangular bandage 108 used to make a sling to support a broken arm around the neck, wire splint 110 used to splint the injury, ice pack 112 used to reduce swelling and pain, and gloves 114 used to minimize contact with body fluids. The eye kit includes an eyewash solution to rinse the eyes, rolled bandage to hold an eye pad in place on the eyes, eye pads which are placed directly over the eyes, paper tape used to hold the eye pads and bandage in place, an ice pack which is used to reduce swelling and pain, and disposable medical gloves to reduce contact with body fluids. The burn pack includes gauze sponges to place on burns, rolled bandage to hold the gauze in place, cloth tape to hold the bandages and gauze in place, and gloves for use to reduce contact with body fluids. The bites and sting pack includes gauze bandages used to control bleeding, cloth tape to hold bandages in place, an ice pack used to reduce swelling and pain, alcohol pads to clean wound areas, tweezers to remove embedded insect parts, and disposable gloves to reduce contact with body fluids.

Figure 7:
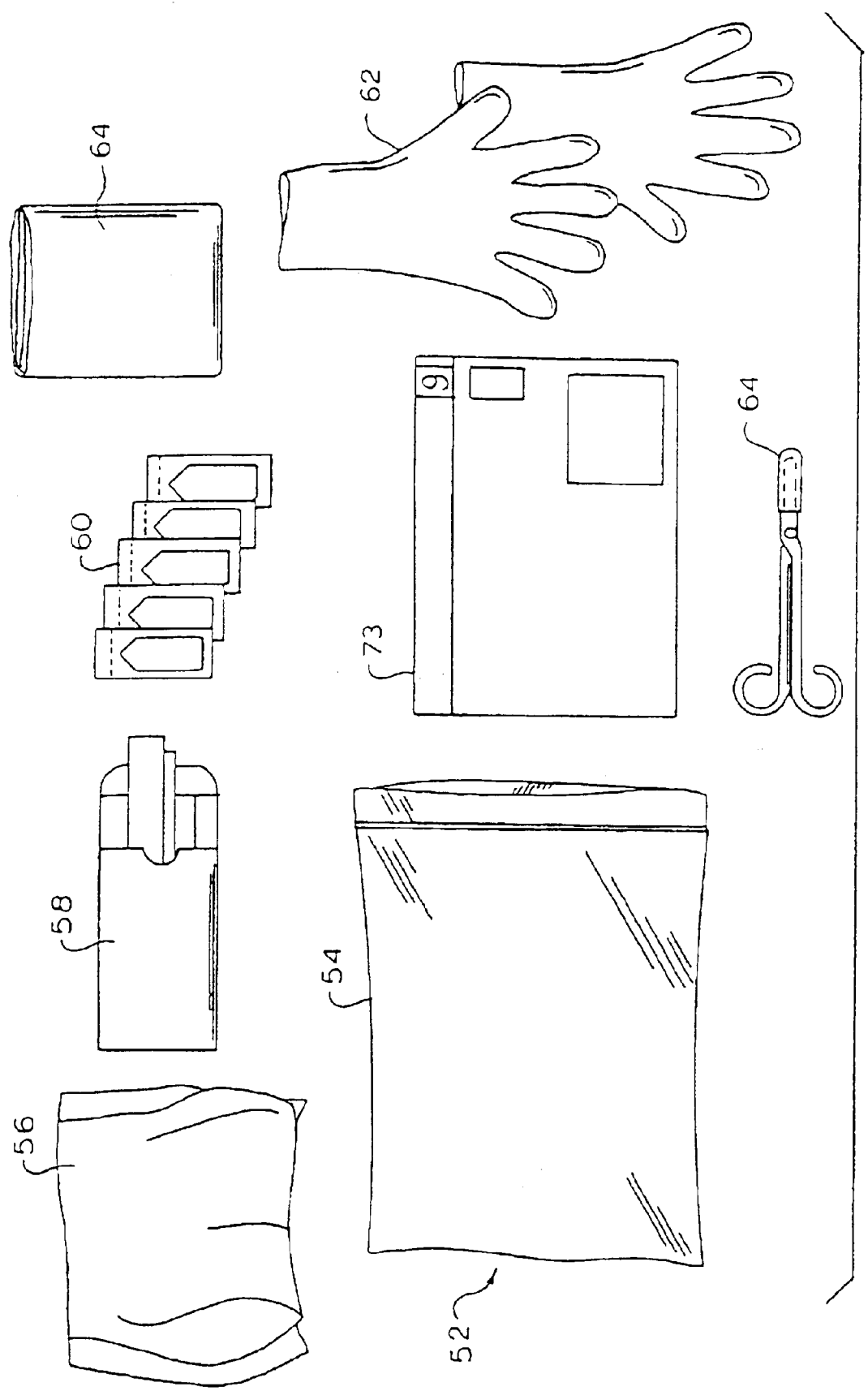
FIG. 7 is an exploded view of the extra pack of the first aid kit of FIG. 1.

In addition to the individual packs targeted for different types of first aid situations, as seen in FIG. 7, an extras pack 52 can be provided. The extras pack 52 includes a reusable container 54 which allows the user to store additional medical product supplies which are useful in a variety of first aid situations, such as, for example, an ice pack 56, bandages 58, ointment 60, disposable gloves 62, scissors 64, and a disposal bag 66. The user can add to the extras pack 52 user specific medical products such as, for example, asthmatic medicine for asthma sufferers, pain medication and the like.

Figure 8:
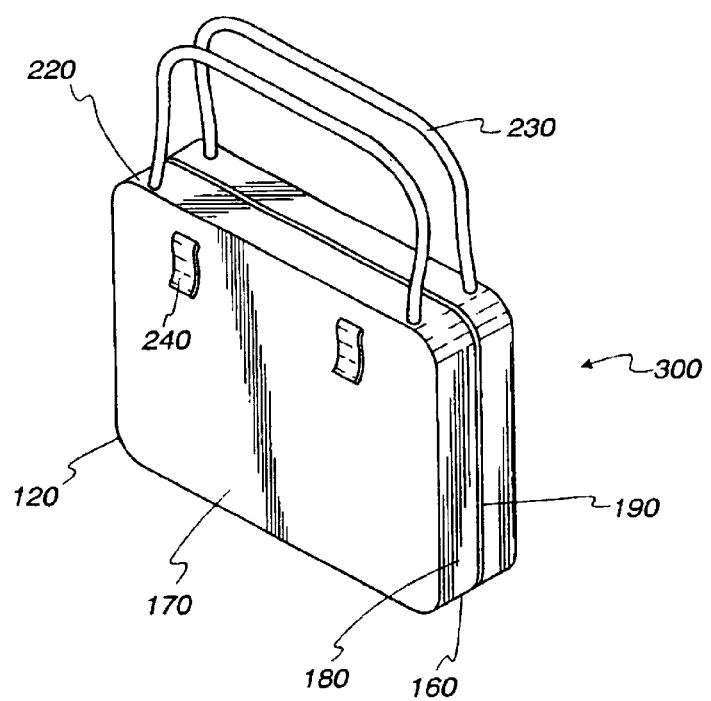
FIG. 8 is a perspective view of an alternate embodiment made in accordance with the principles of the present invention.

Referring to FIG. 8, a perspective view of the first aid kit 300 made in accordance with an alternate embodiment of the first aid kit is depicted. The first aid kit 300 is carried in a case 120 which has a base 160, a top 220, two sides 170, and two ends 180. Preferably, the first aid kit 300 is made of a flexible material such as nylon.

To aid in carrying the first aid kit 300, a handle 230 may be provided, which enables the user to carry the first aid kit in a generally horizontal orientation. Additionally, two belt loop like handles 240 can be provided on the side 170 for carrying the first aid kit 300. Further, a shoulder strap (not shown) can be provided alone or in combination with a handle. The top 220 and the ends 180 may be intersected by a closure means 190 for enabling quick access to the contents of the kit 300. In a preferred embodiment, the closure means 190 consists of a zipper, which runs from the base 160, along the ends 180 and the top 220. The base 160 may be secured to the side 170 and ends 180 by a seam, for example.

Figure 9:
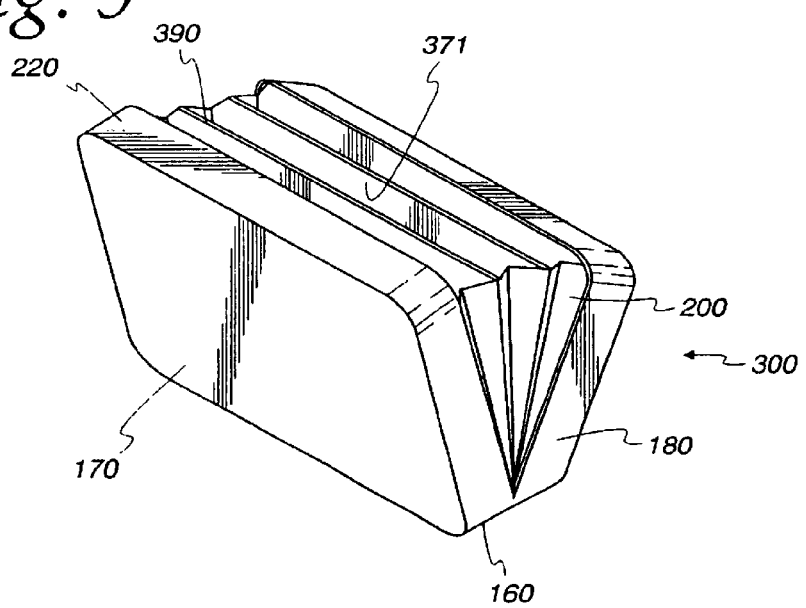
FIG. 9 is a perspective view of the first aid kit of FIG. 8 in an open position.

Referring to FIG. 9, interior sidewalls 200 are connected to the interior of sides 170 to define an interior. The interior comprises a plurality of dividers 390, attached to each sidewall, thus defining a plurality of compartments 371 arranged in an accordion type columnar array. The sidewalls 200 are flexible, and are adapted to allow contents of different thickness can fit into each of the compartments 371. Additionally, the flexible sidewalls 200 provide the accordion style columnar array with its expanding and contracting properties. Each compartment 371 is sequentially oriented in front of the subsequent compartment in the accordion style columnar array.

The accordion style columnar array design permits the compartments 371 to expand to fully occupy the interior. Preferably, each compartment 371 is generally rectangular in shape. When closed, the first aid kit 300 is a very compact carrying case. However, upon opening the first aid kit 300, surprisingly, what is presented to the responder is a first aid kit designed such that it allows the responder to rapidly and completely visualize all of the packs (not shown) and supplies contained in the compartments 371 simultaneously as they are fanned out in front of them, organized by injury. When the first aid kit 300 is closed, the contents can be carried in a compact, portable, unit. The first aid kit 300 may be adapted to rest on the base 160 both in the open and closed positions. The base 160 can be adapted to limit the outward expansion of the accordion style columnar array. Such expansion provides for the rapid access to the contents of the array. Alternately, the front and rear sides 170, 180 may be directly attached to each other, and to the sidewalls 200.

In addition to the icons for breathing, bleeding, and the like, the present invention may also incorporate causative indicating graphics such that the cause of the injury is readily apparent to a user upon viewing the graphic. Causative indicating graphics may be icons, examples of which may include a lightning bolt depicting electrical shock, a sunbeam depicting heatstroke or exhaustion, a gun depicting gunshot wounds, or a knife depicting knife wounds.

Therefore, if a person is bleeding from the result of a gunshot wound, the present invention's unique design directs the primary responder to the bleeding pack and all the responder needs to do is look for the gun icon and the instructions will guide the responder on how to use the products to care for the injured patient. Therefore, even if the responder was to respond to the bleeding first, this design is advantageous because it ensures that, regardless of the visible injury, basic life support checks are performed first on every victim. Therefore, instead of management of a condition, i.e. bleeding, the present invention manages the cause of the bleeding, i.e. gunshot.

The first aid kit of the present invention is also useful for environmental specific first aid needs such as home use, auto use and pet first aid. To aid in the consumer and pet first aid areas (two areas where the user is likely to have less formal training), the first aid kit of the present invention may incorporate packs specifically addressing first aid needs for the home, auto, or for pets.

Figure 10:
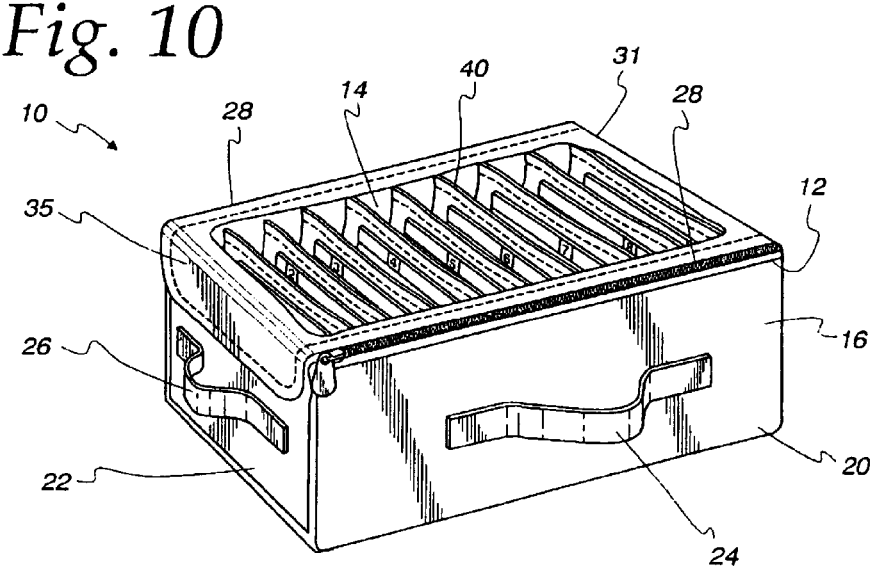
FIG. 10 is a view illustrating an alternate embodiment of the present invention.

Referring to FIG. 10, in a further embodiment, a first aid kit for children for example, may include, a "see through" top. The top is preferably made from a material known in the art from clear to hazy which are sufficient to provide enclosure, yet allow a person responding to an emergency situation to instantly assimilate the colors and icons depicting injuries and correspond the injury with a response action.

The first aid kit 10 is carried in a case 12 that has a top 14 and a base 16 having a bottom, two sides 20, and two ends 22. The sides 20 of the base 16 are generally rectangular and the ends 22 of the base 16 are generally square. The top 14 is secured to the base 16 by use of a closure means for enabling quick access to the contents of the first aid kit 10. In this embodiment, as illustrated in FIG. 10, the top 14 is a see-through top.

Figure 11:
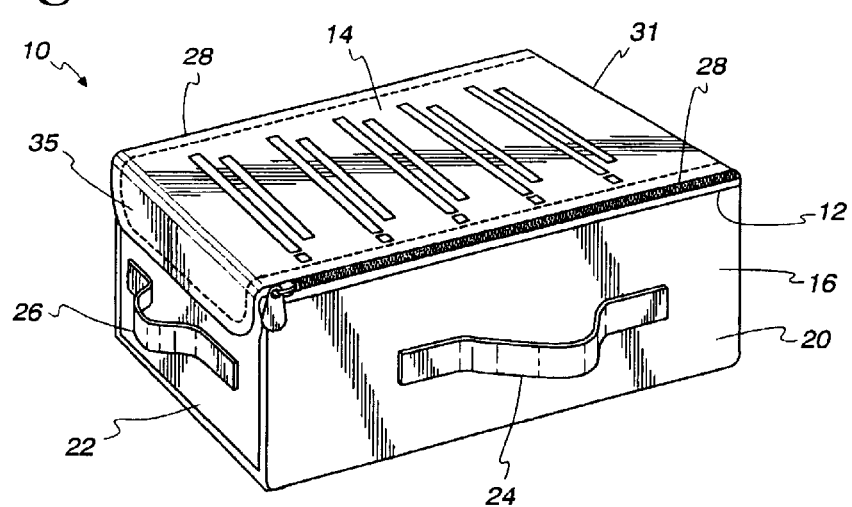
FIG. 11 is a view illustrating an alternate embodiment of the present invention.

In yet a further embodiment, the organizational scheme of the kit can be printed on the top, as shown in FIG. 11. The first aid kit 10 is carried in a case 12 that has a top 14 and a base 16 having a bottom, two sides 20, and two ends 22. The sides 20 of the base 16 are generally rectangular and the ends 22 of the base 16 are generally square. The top 14 is secured to the base 16 by use of a closure means for enabling quick access to the contents of the first aid kit 10. In this embodiment, as illustrated in FIG. 11, the top 14 is printed with the organizational scheme of the first aid kit, depicting the organization of the packs contained therein, such that the kit cover serves as a template of the location of each pack contained in the kit.

Referring back to FIG. 3, in a further embodiment, each pack 40 may be mechanically keyed to a specific compartment 37. A pack 40, for example, may be of a size that only fits in a particular compartment 37. For example, the BLUE pack can have a different shape and size than the PURPLE, RED or YELLOW packs, thereby ensuring that the packs are always placed in the first aid kit 10 in a predetermined order. Accordingly, the order of placement of the packs 40 within the first aid 10, for example, can be arranged so that a pack 40 providing treatment for the most serious injury is placed in the front of the first aid kit 10. The remaining packs 40 can be arranged thereafter in a decreasing order of injury seriousness, with the pack containing supplies for the treatment of the least serious injury being placed in the rear of the first aid kit 10. It should be understood the front of the first aid kit is to mean that part of the first aid kit closest to a responder accessing the contents of the first aid kit 10. The rear of the first aid kit 10 is that part of the first aid kit farthest away from a responder accessing the contents of the first aid kit 10.

In yet a further embodiment, to assist users who are visually impaired, enlarged print or Braille characters may be included on pack labels and overview cards.

What is claimed is:

1. A first aid kit comprising:

a carrying case defining an interior which includes means for providing quick access to the interior, the carrying case having a plurality of compartments in a card catalogue/file cabinet-like array;

a plurality of packs, carried in the compartments, each pack being designated by a descriptive label, and each of the packs containing a plurality of first aid products for the management of a particular first aid situation and arranged according to a system wherein the packs are aligned in the case starting from a position where an emergency responder is located relative to the case in the order of: a pack containing products for the management of a breathing first aid situation, a pack containing products for the management of a bleeding first aid situation, a pack containing products for the management of a shock first aid situation, a pack for the management of a head and spine first aid situation, a pack for the management of a bone first aid situation, a pack for the management of a burn first aid situation, and then a pack for the management of a bites and stings first aid situation; and an instructional card within each pack, the instructional card having a corresponding descriptive label with the pack and bearing instructions for use of the contents within the pack for the first aid situation described on the label and instructing the user to check a set of vital indicators of a person requiring first aid.

2. The first aid kit of claim 1 further providing a guidebook that includes instructions regarding the products contained in each pack and wherein the instructions are set forth in graphical depictions to guide the use in the use of the products of each pack.

3. The first aid kit of claim 2 wherein the instructional cards contained in the packs are capable of being combined to form a duplicate guide book such that a secondary responder can read the matching instructions on the instructional card to a primary responder who can follow the guidebook graphical depictions simultaneously.

4. The first aid kit of claim 1 wherein each pack includes a causative indicating graphic.

5. The first aid kit of claim 4 wherein the causative indicating graphic is as icon depicting the cause of the first aid situation.

6. The first aid kit of claim 1 wherein each pack is designated a size or shape which is different than the size or shape designated to the remaining packs.

7. The first aid kit of claim 1 further wherein the carrying case is an accordion style collapsible case.

8. A method for arranging the contents of a first aid kit comprising the steps of:

assembling a collection of packs containing products for the management of particular first aid situations;

ranking the seriousness of the first aid situation to be managed using each pack in an order beginning with the most serious and ending with the least serious first aid situation;

placing the pack for the management of the most serious first aid situation in a front compartment of the first aid kit; and arranging the remaining packs in a card catalogue/file cabinet-like array and in an order of descending seriousness in the first aid kit behind the pack for the management of the most serious first aid situation.

9. The method of claim 8 further comprising the steps of:

adding a new pack for the management of a new first aid situation by:

determining a seriousness ranking of the new first aid situation;

comparing the seriousness ranking of the new first aid situation to the seriousness ranking of the packs arranged in the first aid kit;

locating the pack for the management of the first aid situation that is ranked as the next less serious situation as compared to the new situation;

placing the new pack in front of the pack for the management of the first aid situation ranked as the next serious situation as compared to the new situation.

10. A method for the administering first aid comprising the steps of:

identifying a victim requiring first aid, obtaining a first aid kit, the first aid kit having:

a carrying case defining an interior which includes means for providing quick access to the interior, the carrying case having a plurality of compartments in a card catalogue/file cabinet-like array;

a plurality of packs, carried in the compartments, each pack being designated by a descriptive label, and each of the packs containing a plurality of first aid products for the management of a particular first aid situation and arranged according to a system wherein the packs are aligned starting from an emergency responder in the order of: a pack containing products for the management of a breathing first aid situation, a pack containing products for the management of a bleeding first aid situation, a pack containing products for the management of a shock first aid situation, a pack for the management of a head and spine first aid situation, a pack for the management of a bone first aid situation, a pack for the management of a burn first aid situation, and then a pack for the management of a bites and stings first aid situation; and an instructional card within each pack, the instructional card having a corresponding descriptive label with the pack and bearing instructions for use of the contents within the pack for the first aid situation described on the label and instructing the user to check a set of vital indicators of a person requiring first aid;

identifying a pack of products within the first aid kit by matching the first aid situation with the pack of products bearing an icon depicting the first aid situation;

managing the first aid situation according to the instructions printed on a card contained within the pack of products for the management of that particular first aid situation; and replacing the pack of products for that particular first aid situation with an identical pack of products.

* * * * *

UNITED STATES PATENT AND TRADEMARK OFFICE
CERTIFICATE OF CORRECTION

PATENT NO. : 6,957,738 B2
DATED : October 25, 2005
INVENTOR(S) : David A. Hammond It is certified that error appears in the above-identified patent and that said Letters Patent is hereby corrected as shown below:

Column 9,
Line 36, change "guide the use" to -- guide the user --.

Signed and Sealed this

Sixteenth Day of May, 2006

JON W. DUDAS
*Director of the United States Patent and Trademark Office*